(12) United States Patent
Gutterman (10) Patent No.: US 11,351,281 B2
(45) Date of Patent: Jun. 7, 2022

(54) DEVICES AND METHODS FOR STERILIZING PROTECTIVE FACIAL MASKS AND MEDICAL GARMENTS USING MICROWAVE ENERGY

(71) Applicant: R. Gutterman Resources and Holdings Ltd., Kfar Daniel (IL)

(72) Inventor: Ron Gutterman, Kfar Daniel (IL)

(73) Assignee: R. Gutterman Resources and Holdings Ltd., Kfar Daniel (IL)

( * ) Notice: Subject to any disclaimer, the term of this patent is extended or adjusted under 35 U.S.C. 154(b) by 0 days.

(21) Appl. No.: 17/489,839

(22) Filed: Sep. 30, 2021

(65) Prior Publication Data

US 2022/0105213 A1    Apr. 7, 2022

(30) Foreign Application Priority Data

Oct. 2, 2020    (EP) .................................... 20199952

(51) Int. Cl.
*A61L 2/12* (2006.01)
*A61L 2/26* (2006.01)
*A61L 2/07* (2006.01)

(52) U.S. Cl.
CPC *A61L 2/12* (2013.01); *A61L 2/07* (2013.01); *A61L 2/26* (2013.01); *A61L 2202/122* (2013.01); *A61L 2202/15* (2013.01); *A61L 2202/26* (2013.01)

(58) Field of Classification Search
CPC ..... A61L 2/07; A61L 2/12; A61L 2/26; A61L 2202/122; A61L 2202/15; A61L 2202/26
See application file for complete search history.

(56) References Cited

U.S. PATENT DOCUMENTS

| 1,983,390 | A | * | 12/1934 | Mueller | A61L 2/07 422/303 |
| 4,544,529 | A | * | 10/1985 | Hoeck | A61L 2/07 422/303 |
| 2004/0040586 | A1 | | 3/2004 | Kumar | |

FOREIGN PATENT DOCUMENTS

| CN | 105709251 A | 6/2016 |
| GB | 2134788 A | 8/1984 |

\* cited by examiner

*Primary Examiner* — Timothy C Cleveland
(74) *Attorney, Agent, or Firm* — Reuven K. Mouallem; FlashPoint IP Ltd.

(57) ABSTRACT

The present invention discloses devices and methods for sterilizing protective facial masks and medical garments using microwave energy. Devices include: a fabric sterilization unit for serving as a housing; a water basin disposed inside the sterilization unit, the water basin configured for generating steam in the water basin when exposed to the microwave energy; a nozzle array plate disposed inside the sterilization unit above the water basin, the nozzle array plate configured for increasing the steam pressure by restricting steam escape; an array of steam-jet nozzles with angled upper sections configured for directing a flow of high-pressure, high-temperature steam jets exiting from the nozzles toward at least one fabric material; and material holders for individually positioning and supporting the material such that the steam jets impinge on the material for: sterilizing the material from microbial transmission and/or reproduction; and enabling reusability of the material as suitable Personal Protective Equipment (PPE).

18 Claims, 8 Drawing Sheets

Exemplary Embodiment

Exemplary Embodiment

Exemplary Embodiment

Exemplary Embodiment

DEVICES AND METHODS FOR STERILIZING PROTECTIVE FACIAL MASKS AND MEDICAL GARMENTS USING MICROWAVE ENERGY

CROSS REFERENCE TO RELATED APPLICATIONS

This patent application claims priority under 35 U.S.C. § 119(a) to European Patent Application No. EP 20199952.1, filed Oct. 2, 2020, which is hereby incorporated by reference in its entirety.

FIELD AND BACKGROUND OF THE INVENTION

The present invention relates to devices and methods for sterilizing protective facial masks and medical garments, including surgical masks, using microwave energy.

Following the outbreak of the worldwide pandemic novel coronavirus in late 2019, referred to as COVID-19, along with social distancing and hand sanitation, the wearing of protective facial masks (including scarves and other ad hoc means) has become ubiquitous throughout the world in order to mitigate, and hopefully eliminate, this scourge on humanity. The civilian populations of over 100 countries around the world were instructed (and in many places mandated) to wear protective facial masks in public areas and workplaces. While there is much debate about its function and effectivity, the facial mask primarily serves as a means of filtering the exhaled air of the wearer to limit and/or prevent emission of viral particles into the surroundings.

Various types of masks are available from simple cloth masks to others having unique components providing additional benefits. The common thread of the majority of facial masks (excluding plastic facial shields) is that the primary component is based on a fabric and/or polymeric fabric material. While functionality, ergonomics/wearability, and aesthetics are attributes that differentiate masks that are being marketed, other key aspects are the cost and reusability of such masks.

Cost and reusability are qualities that go hand in hand. Beside the initial manufacturing cost, if a mask can be effectively reused, the net cost of the mask over time is reduced when compared to the alternative of disposable masks. However, reusability hinges greatly on whether a used mask (i.e., a mask that has potentially been exposed to a viral environment) can be effectively cleaned without impacting the mask's integrity to provide continued protection. In this regard, the "cleaning" of the mask becomes a much more stringent criterion than it is colloquially used.

According to the United States Centers for Disease Control and Prevention (CDC), the various terms have significantly different meanings. Cleaning removes germs, dirt, and other impurities from surfaces, but doesn't necessarily kill them. Sanitizing lowers the number of germs on surfaces or objects, either by killing them or removing them, to a safe level, according to public health standards or requirements. Disinfecting kills germs on surfaces or objects.

While disinfection and sterilization are both forms of decontamination that are frequently used interchangeably, it is important to point out how they differ in the context of COVID-19. A disinfectant kills vegetative microorganisms, but not spores, such as a protective membrane that protects the microorganisms from disinfectant chemicals. Sterilization kills all life forms, including the hard-to-kill spores. An asepsis is the absence of bacteria, viruses, and other microorganisms as exists in a sterile environment, blocking the possibility of any microbial transmission or reproduction. As such, achieving the strict requirements of a sterilized facial mask while maintaining its effectivity as a suitable form of Personal Protective Equipment (PPE) is a challenge.

In practice, the human respiratory process is accompanied by the exhalation of a high level of moisture that typically creates a moist area of a worn facial mask. The breathing process for a mask wearer results in the trapping of odors, saliva, and pathogens in the facial mask, and not releasing such agents into the free air. The facial mask serves as a filter for the exhaled air as well as the inhaled air, reducing and/or preventing the entry of pathogenic droplets from surrounding individuals as well as other contaminated particles such as dust. The pathogenic penetrability of a facial mask is the basis for assessing the mask's suitable filtering potential.

The COVID-19 pandemic has created a situation in which the majority of the world's population is routinely required to wear a facial mask, necessitating an effective and easy way to "clean" the pathogenicity of facial masks.

Microwave energy has been used in numerous devices for various everyday drying and heating applications from accelerating conventional clothing dryers, disinfecting baby bottles, and cleaning hospitality bedding and mattresses to decontaminating envelopes and packages, and deactivating virus and bacteria by microwave exposure in the presence of various chemical agents.

The common microwave oven, relying on using rapid internal volumetric heating, with some alteration has been shown to be a suitable replacement to conventional autoclaves. Thus, in the wake of the initial outbreak of COVID-19, many individuals published homemade approaches to cleaning a facial mask by using a household microwave oven. Given the base fabric constituent, many such attempts resulted in the mask burning or catching on fire. Other attempts to include water in the oven resulted in wetting the mask, bringing the effective reusability into question. In all such ad hoc methods, the resultant level of "cleaning" of the facial mask was not clearly established.

The challenge in using microwave energy to sterilize materials such as fabric-based masks and other medical garments for virus deactivation thus includes: (1) preventing the material from being burnt, singed, or otherwise compromised; (2) achieving a sufficient temperature of the material to cause true sterilization; and (3) preventing the material from becoming wet to avoid degradation of the material integrity and/or pore structure. It is noted that the wetting of the material can cause the spread of contamination points throughout the material, as well as limit the maximum temperature achieved throughout the material.

It would be desirable to have devices and methods for sterilizing protective facial masks and medical garments, including surgical masks, using microwave energy. Such devices and methods would, inter alia, overcome the various limitations mentioned above.

SUMMARY

It is the purpose of the present invention to provide devices and methods for sterilizing protective facial masks and medical garments, including surgical masks, using microwave energy.

It is noted that the term "exemplary" is used herein to refer to examples of embodiments and/or implementations, and is not meant to necessarily convey a more-desirable use-case. Similarly, the terms "alternative" and "alternatively" are used herein to refer to an example out of an assortment of contemplated embodiments and/or implementations, and is not meant to necessarily convey a more-desirable use-case. Therefore, it is understood from the above that "exemplary" and "alternative" may be applied herein to multiple embodiments and/or implementations. Various combinations of such alternative and/or exemplary embodiments are also contemplated herein.

Embodiments of the present invention provide a fabric sterilization unit having an integral water basin, an array of directed-flow steam-jet nozzles, and material holders for supporting and positioning the fabric material (e.g., for use as PPE) appropriately in relation to the steam-jet nozzles. The directed flow of microwave-generated steam exiting the nozzles during operation produces high-pressure, high-temperature steam jets without any water droplets, enabling sterilization without causing burning or singeing of the fabric material and without wetting the fabric material.

Embodiments of the present invention further provide the fabric sterilization unit with a canopy cover for concentrating the amount of steam in the unit, as well as the exposure temperature inside the unit, during operation. The canopy cover may include canopy ventilation slots to release excessive steam pressure and moisture in the unit during operation in order to prevent wetting of the fabric material. The canopy cover may further include formed ridges along its interior to act as a drainage system to wick away water droplets that can condense on the cover, averting the potential for the droplets to drip onto the fabric material below. The formed ridges wick away any liquid water toward the walls of the unit, and return the liquid down into the water basin.

Therefore, according to the present invention, there is provided for the first time a device for sterilizing protective facial masks and medical garments using microwave energy, the device including: (a) a fabric sterilization unit for serving as a housing; (b) a water basin disposed inside the fabric sterilization unit, the water basin configured for generating steam from water in the water basin when exposed to the microwave energy; (c) a nozzle array plate disposed inside the fabric sterilization unit above the water basin, the nozzle array plate configured for increasing the pressure of the steam by restricting escape of the steam; (d) an array of steam-jet nozzles configured for directing a flow of high-pressure, high-temperature steam jets exiting from the steam-jet nozzles toward at least one fabric material, wherein the steam-jet nozzles have angled upper sections to constrict the high-pressure, high-temperature steam jets to be free of any liquid water droplets upon exiting due to the high-pressure differential between the water basin below the nozzle array plate and the interior of the fabric sterilization unit above the nozzle array plate; and (e) material holders for individually positioning and supporting at least one fabric material in relation to the array of steam-jet nozzles adapted such that the high-pressure, high-temperature steam jets impinge across the surfaces of at least one fabric material for: (i) sterilizing at least one fabric material from microbial transmission and/or reproduction; and (ii) enabling reusability of at least one fabric material as suitable Personal Protective Equipment (PPE).

Alternatively, the water basin is an integral component of the fabric sterilization unit.

Alternatively, the fabric sterilization unit and the material holders are adapted for accommodating and supporting at least one fabric material as a constituent of a surgical mask.

Alternatively, the angled upper sections of the steam-jet nozzles are further configured to prevent undesirable circulation currents to form in the flow during operation.

Alternatively, the high-pressure, high-temperature steam jets are adapted to perform the sterilizing without burning, singeing, wetting, or otherwise compromising at least one fabric material.

Alternatively, the device further includes: (f) a canopy cover integrally connected to the fabric sterilization unit, the canopy cover configured for increasing the internal pressure and internal temperature of the fabric sterilization unit during operation.

Most alternatively, the canopy cover includes at least one ventilation slot configured for: (i) allowing excess moisture to exit the fabric sterilization unit during operation; and (ii) preventing condensation on the interior surface of the canopy cover.

Most alternatively, the canopy cover includes at least one drainage ridge formed along the inner contour of the canopy cover, and wherein at least one drainage ridge configured for wicking away any liquid water that forms on the canopy cover toward the walls of the fabric sterilization unit and returning to the water basin during operation in order to prevent any condensed water droplets from dripping onto at least one fabric material during operation.

Most alternatively, the canopy cover is adapted to remove excess humidity as gaseous moisture from the interior of the fabric sterilization unit due to the relatively lower temperature of the surfaces of the fabric sterilization unit relative to the internal temperature of the steam generated by the microwave energy.

According to the present invention, there is provided for the first time a method for sterilizing protective facial masks and medical garments using microwave energy, the method including the steps of: (a) providing a fabric sterilization unit for serving as a housing and a water basin inside the fabric sterilization unit; (b) generating steam from water in the water basin by exposing the fabric sterilization unit to the microwave energy; (c) increasing the pressure of the steam by restricting escape of the steam by disposing a nozzle array plate inside the fabric sterilization unit above the water basin; (d) directing a flow of high-pressure, high-temperature steam jets exiting from an array of steam-jet nozzles in the nozzle array plate toward at least one fabric material, wherein the steam-jet nozzles have angled upper sections to constrict the high-pressure, high-temperature steam jets to be free of any liquid water droplets upon exiting due to the high-pressure differential between the water basin below the nozzle array plate and the interior of the fabric sterilization unit above the nozzle array plate; and (e) individually positioning and supporting at least one fabric material, using material holders, in relation to the array of steam-jet nozzles such that the high-pressure, high-temperature steam jets impinge across the surfaces of at least one fabric material; (f) sterilizing at least one fabric material from microbial transmission and/or reproduction; and (g) enabling reusability of at least one fabric material as suitable Personal Protective Equipment (PPE).

Alternatively, the water basin is an integral component of the fabric sterilization unit.

Alternatively, the fabric sterilization unit and the material holders are adapted to accommodate and support at least one fabric material as is a constituent of a surgical mask.

Alternatively, the angled upper sections of the steam-jet nozzles are further configured to prevent undesirable circulation currents to form in the flow during operation.

Alternatively, the step of sterilizing at least one fabric material is performed without burning, singeing, wetting, or otherwise compromising at least one fabric material.

Alternatively, the method further includes the step of: (h) increasing the internal pressure and internal temperature of the fabric sterilization unit during operation by integrally connecting a canopy cover to the fabric sterilization unit.

Most alternatively, the canopy cover includes at least one ventilation slot configured for: (A) allowing excess moisture to exit the fabric sterilization unit during operation; and (B) preventing condensation on the interior surface of the canopy cover.

Most alternatively, the canopy cover includes at least one drainage ridge formed along the inner contour of the canopy cover, and wherein at least one drainage ridge is configured for wicking away any liquid water that forms on the canopy cover toward the walls of the fabric sterilization unit and returning to the water basin during operation in order to prevent any condensed water droplets from dripping onto at least one fabric material.

Most alternatively, the canopy cover is adapted to remove excess humidity as gaseous moisture from the interior of the fabric sterilization unit due to the relatively lower temperature of the surfaces of the fabric sterilization unit relative to the internal temperature of the steam generated by the microwave energy.

These and further embodiments will be apparent from the detailed description and examples that follow.

BRIEF DESCRIPTION OF THE DRAWINGS

The present invention is herein described, by way of example only, with reference to the accompanying drawings, wherein.

DESCRIPTION OF THE ILLUSTRATIVE EMBODIMENTS

The present invention relates to devices and methods for sterilizing protective facial masks and medical garments, including surgical masks, using microwave energy. The principles and operation for providing such devices and methods, according to the present invention, may be better understood with reference to the accompanying description and the drawings.

Figure 1A:
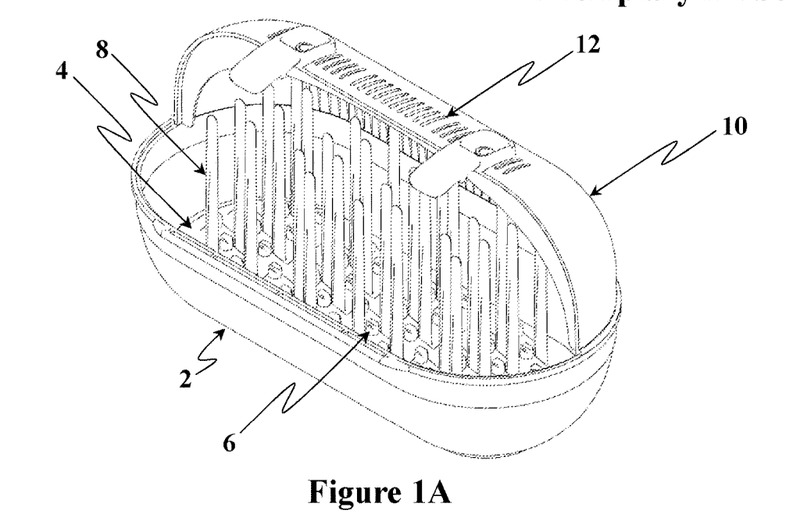
FIG. 1A depicts a perspective view of a partially-open fabric sterilization unit for using with microwave energy, according to embodiments of the present invention.

Referring to the drawings, FIG. 1A depicts a perspective view of a partially-open fabric sterilization unit for using with microwave energy, according to embodiments of the present invention. A fabric sterilization unit 2 having a nozzle array plate 4, steam-jet nozzles 6, material holders 8, an optional canopy cover 10, and optional canopy ventilation slots 12 is shown. A water basin located under nozzle array plate 4 resides in the lower part of fabric sterilization unit 2 (not visible in FIG. 1A, but depicted in FIGS. 4-6).

In operation, fabric sterilization unit 2 is suitably filled with water under nozzle array plate 4. Then, fabric material (e.g., for use as PPE such as facial masks, surgical masks, medical garments, scarves, and gloves) are individually positioned among steam-jet nozzles 6, and supported by material holders 8. Fabric sterilization unit 2 is then inserted into a suitable device for emitting microwave energy (e.g., a common microwave oven). Once water in the basin is heated past its phase-transition temperature, pressure builds under nozzle array plate 4 due to the steam formed.

The microwave-generated gaseous water forms high-pressure, high-temperature steam jets exiting steam-jet nozzles 6 that contain no water droplets. The directed flow of such steam jets at the individually-positioned fabric material serves to simply, quickly, and effectively sterilize the fabric material without burning, singeing, wetting, or otherwise compromising the fabric material, providing antiviral protection and reusability of the fabric material as PPE. Optional canopy cover 10 serves to enhance the effects of fabric sterilization unit 2 by increasing the internal pressure and temperature during operation. Optional canopy ventilation slots 12 serve to allow excess moisture to exit fabric sterilization unit 2 during operation, preventing condensation on the interior surface of canopy cover 10.

Appropriate construction materials for the manufacturing of fabric sterilization unit 2 are only technically limited by the suitability of the construction materials to operate in an environment of microwave energy, high temperature, and high humidity.

Figure 1B:
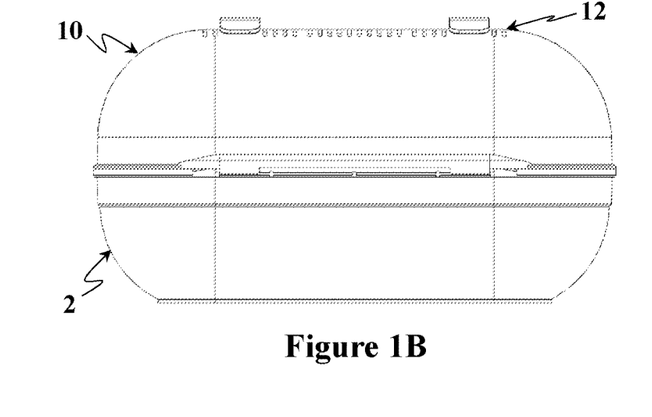
FIG. 1B depicts a side view of the fully-closed fabric sterilization unit of FIG. 1A, according to embodiments of the present invention.
Figure 1C:
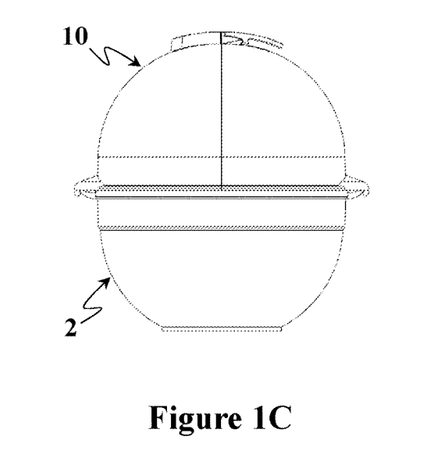
FIG. 1C depicts an end view of the fully-closed fabric sterilization unit of FIG. 1A, according to embodiments of the present invention.
Figure 1D:
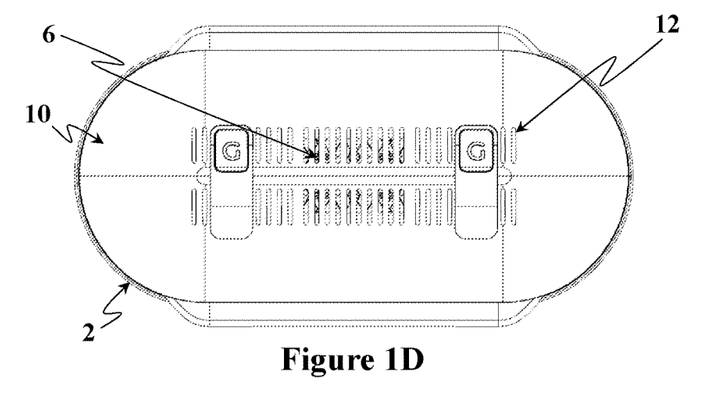
FIG. 1D depicts a top view of the fully-closed fabric sterilization unit of FIG. 1A, according to embodiments of the present invention.

FIG. 1B depicts a side view of the fully-closed fabric sterilization unit of FIG. 1A, according to embodiments of the present invention. FIG. 1C depicts an end view of the fully-closed fabric sterilization unit of FIG. 1A, according to embodiments of the present invention. FIG. 1D depicts a top view of the fully-closed fabric sterilization unit of FIG. 1A, according to embodiments of the present invention. Steam-jet nozzles 6 can be seen through canopy ventilation slots 12 of FIG. 1D.

Figure 2A:
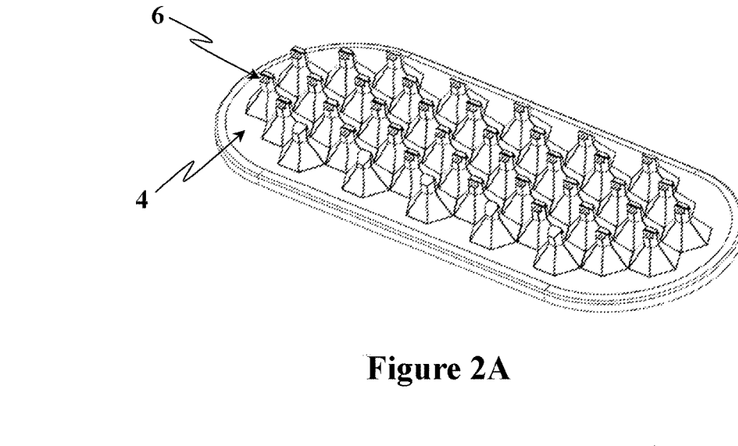
FIG. 2A depicts a perspective view of the nozzle array plate of the fabric sterilization unit of FIG. 1A with the material holders hidden, according to embodiments of the present invention.
Figure 2B:
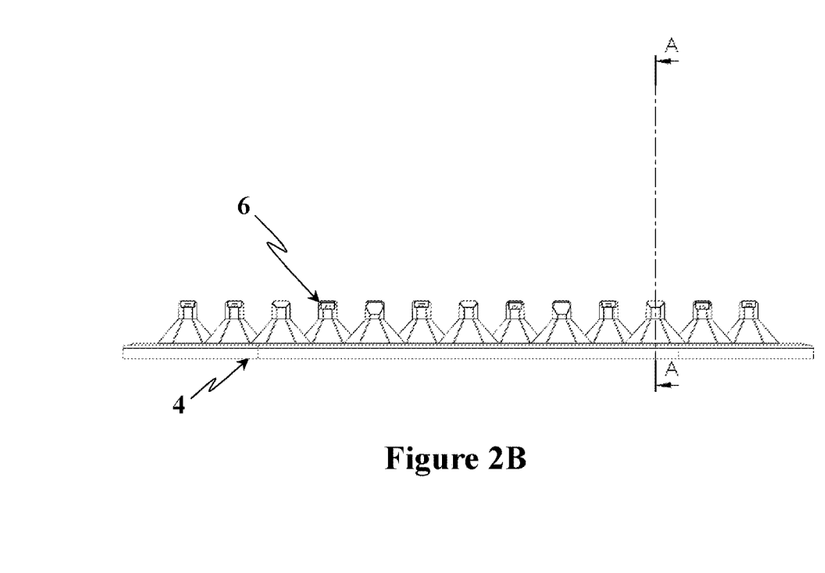
FIG. 2B depicts a side view of the nozzle array plate of FIG. 2A with section line A-A, according to embodiments of the present invention.
Figure 2C:
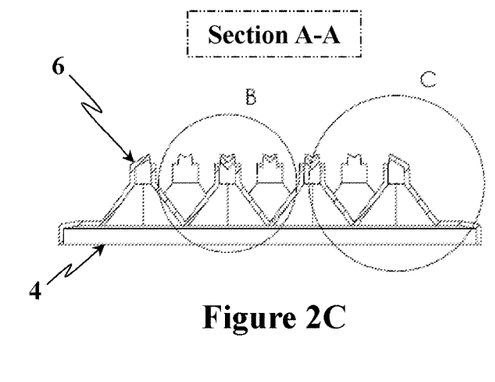
FIG. 2C depicts a section view of the nozzle array plate of FIG. 2B along section line A-A, according to embodiments of the present invention.
Figure 2D:
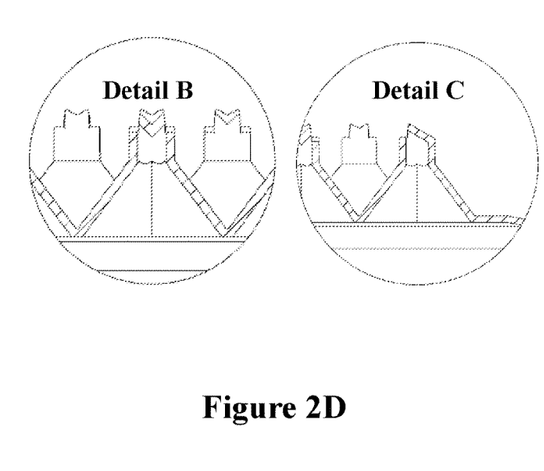
FIG. 2D depicts a detail view of details B and C of FIG. 2C showing the steam-jet nozzles, according to embodiments of the present invention.

FIG. 2A depicts a perspective view of the nozzle array plate of the fabric sterilization unit of FIG. 1A with the material holders hidden, according to embodiments of the present invention. FIG. 2B depicts a side view of the nozzle array plate of FIG. 2A with section line A-A, according to embodiments of the present invention. FIG. 2C depicts a section view of the nozzle array plate of FIG. 2B along section line A-A, according to embodiments of the present invention. FIG. 2D depicts a detail view of details B and C of FIG. 2C showing the steam-jet nozzles, according to embodiments of the present invention.

Optionally, as shown in Detail B and Detail C of FIGS. 2C and 2D, steam-jet nozzles 6 can be configured to direct high-pressure, high-temperature steam jets at various angles during operation, depending on the application and configuration of material holders 8. For example, a certain type of fabric material used may require such steam jets to impinge on its surfaces at various heights and on both sides. Detail B shows an exemplary directed steam-jet nozzle 6 with two exit ports at a given angle. Detail C shows an exemplary directed steam-jet nozzle 6 with only one exit port at a given angle.

For example, steam-jet nozzle 6 as shown in Detail C may be positioned in nozzle array plate 4 at the end of a row of steam-jet nozzles 6 if there is no opposing fabric material on the other side of the "C-type" steam-jet nozzle during operation. Or, a C-type steam-jet nozzle may be implemented in applications in which only one side of the fabric material used needs to be exposed to the steam jets, enabling an even higher pressure and temperature of the directed steam jet to be achieved during operation.

Steam-jet nozzle 6 are depicted in Details B and C of FIGS. 2C and 2D with angled "roofs" as an optional feature to prevent undesirable circulation currents to form in the exiting steam jets during operation, potentially caused by flat-roofed configurations.

Figure 3A:
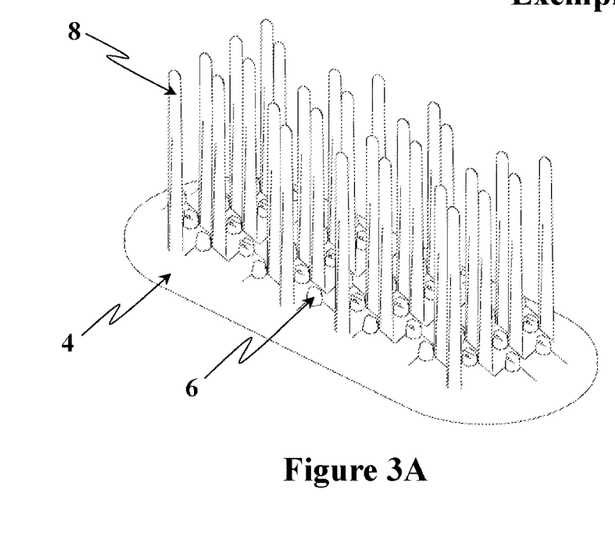
FIG. 3A depicts a perspective view of the nozzle array plate of the fabric sterilization unit of FIG. 1A with the material holders shown, according to embodiments of the present invention.
Figure 3B:
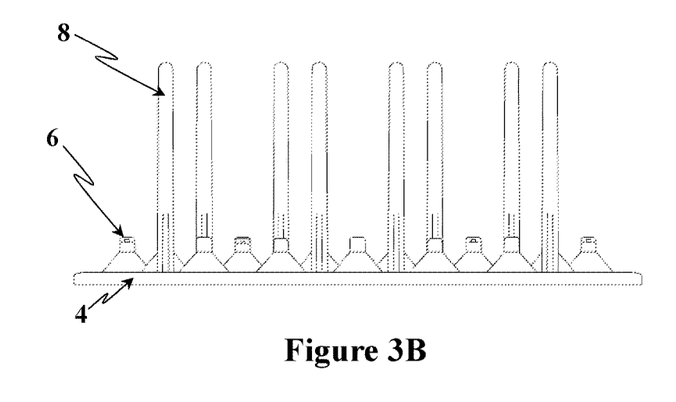
FIG. 3B depicts a side view of the nozzle array plate of FIG. 3A, according to embodiments of the present invention.
Figure 3C:
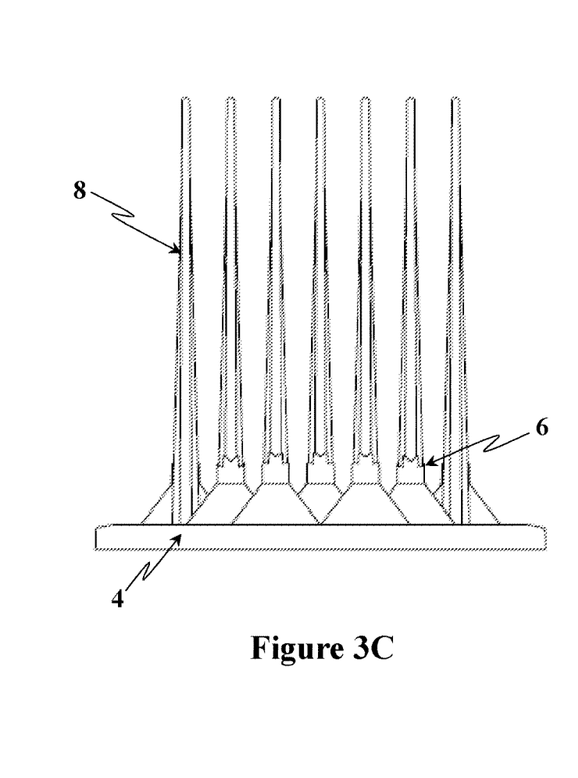
FIG. 3C depicts an end view of the nozzle array plate of FIG. 3A, according to embodiments of the present invention.

FIG. 3A depicts a perspective view of the nozzle array plate of the fabric sterilization unit of FIG. 1A with the material holders shown, according to embodiments of the present invention. FIG. 3B depicts a side view of the nozzle array plate of FIG. 3A, according to embodiments of the present invention. FIG. 3C depicts an end view of the nozzle array plate of FIG. 3A, according to embodiments of the present invention. The staggered arrangement of material holders 8 with steam-jet nozzles 6 on nozzle array plate 4 helps to maximize the contact of the impinging directed steam jets with the fabric material during operation.

Figures 4A, 4B:
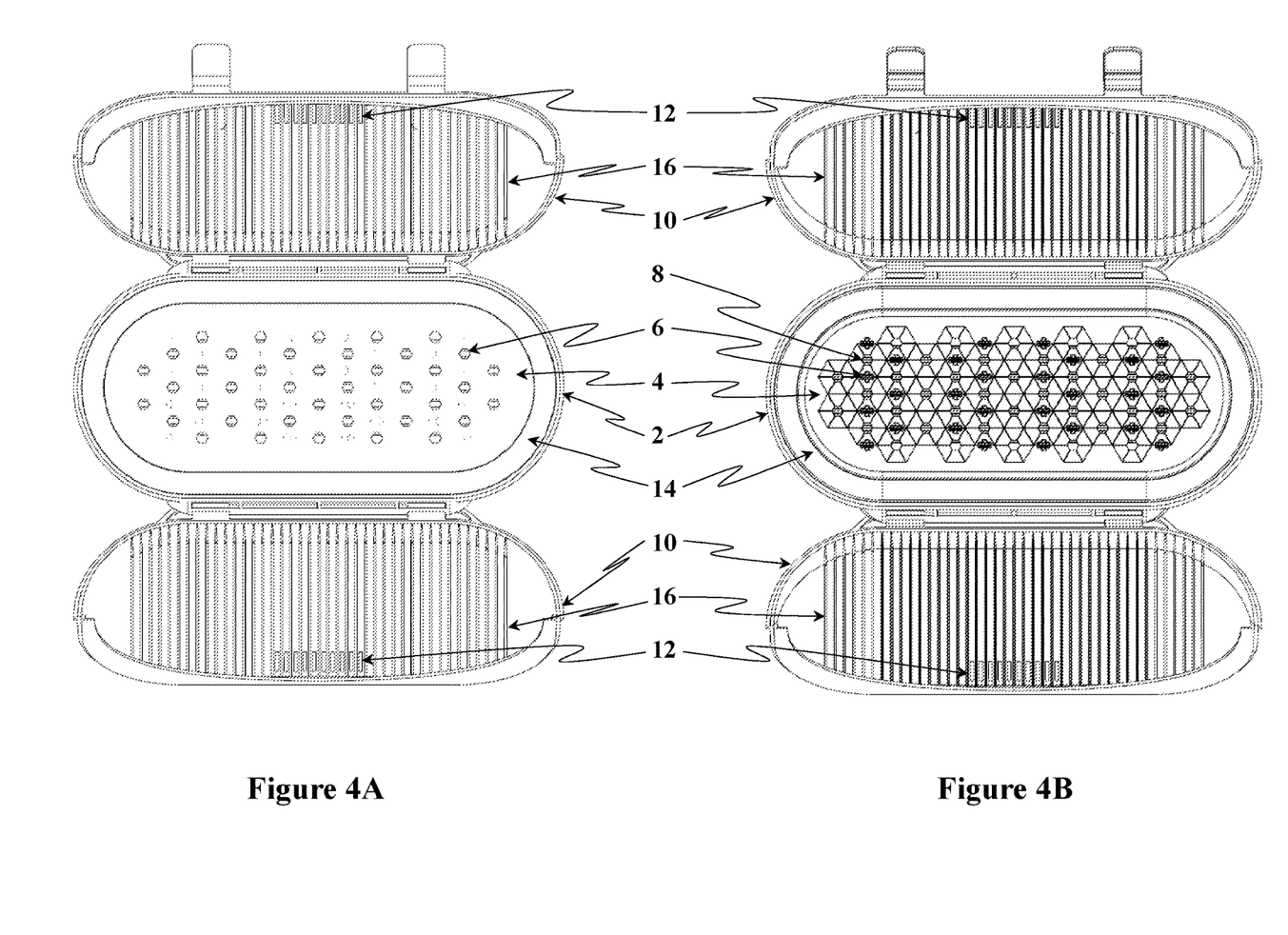
FIG. 4A depicts a top view of the fully-open fabric sterilization unit of FIG. 1A with the material holders hidden, according to embodiments of the present invention.
FIG. 4B depicts a top view of the fully-open fabric sterilization unit of FIG. 1A with the material holders shown, according to embodiments of the present invention.

FIG. 4A depicts a top view of the fully-open fabric sterilization unit of FIG. 1A with the material holders hidden, according to embodiments of the present invention. FIG. 4B depicts a top view of the fully-open fabric sterilization unit of FIG. 1A with the material holders shown, according to embodiments of the present invention. An integral water basin 14 is shown adjoining the interior perimeter of fabric sterilization unit 2 like a moat, allowing for condensed moisture to collect under nozzle array plate 4. Alternatively, a separate water basin can be employed for easy filling.

Optional formed drainage ridges 16 are also shown in FIGS. 4A and 4B along the interior contour of canopy cover 10. Formed drainage ridges 16 enable water droplets that condense on canopy cover 10 to drain down along the cover to integral water basin 14 during operation of fabric sterilization unit 2, preventing fabric materials from becoming wet. The size, shape, and number of formed drainage ridges 16 can be tailored to the application of fabric sterilization unit 2.

Figures 5A, 5B:
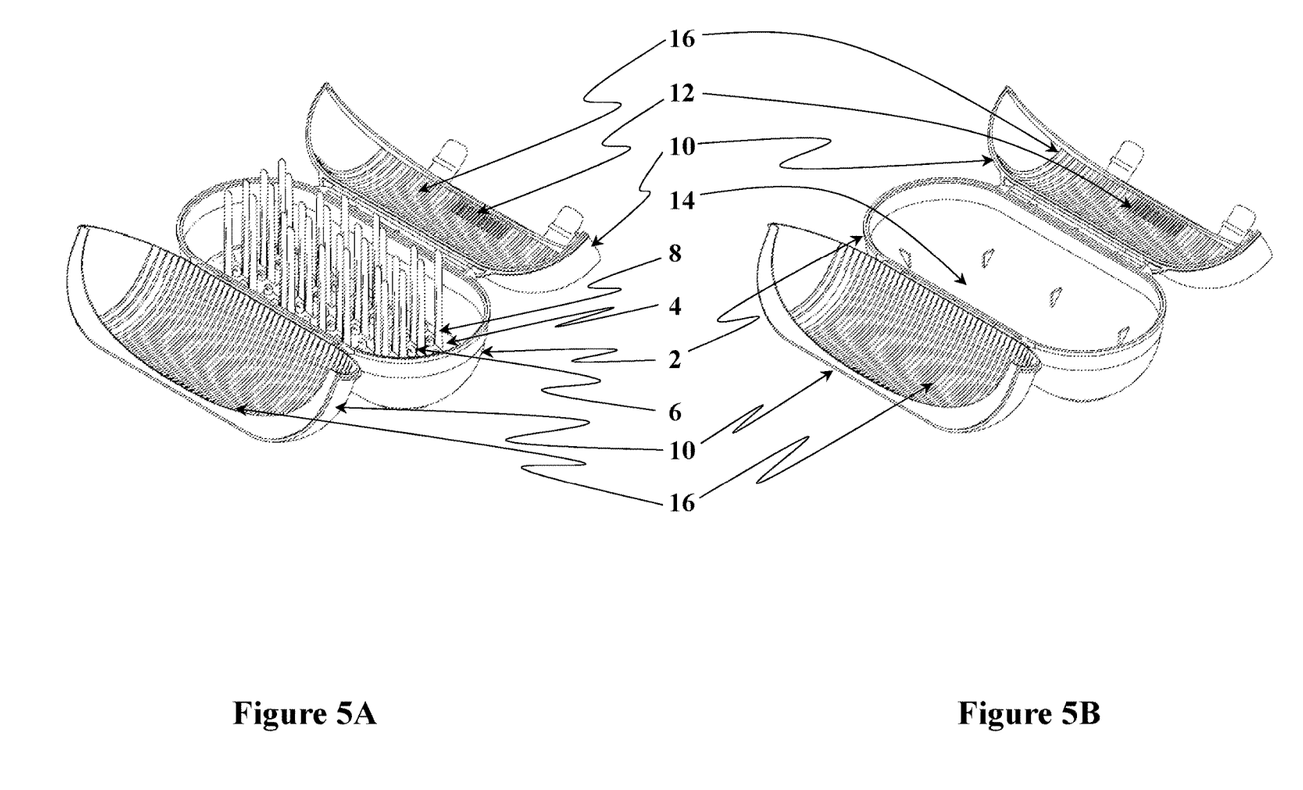
FIG. 5A depicts a perspective view of the fully-open fabric sterilization unit of FIG. 1A with the nozzle array plate shown, according to embodiments of the present invention.
FIG. 5B depicts a perspective view of the fully-open fabric sterilization unit of FIG. 1A with the nozzle array plate hidden, revealing the integral water basin, according to embodiments of the present invention.

FIG. 5A depicts a perspective view of the fully-open fabric sterilization unit of FIG. 1A with the nozzle array plate shown, according to embodiments of the present invention. FIG. 5B depicts a perspective view of the fully-open fabric sterilization unit of FIG. 1A with the nozzle array plate hidden, revealing the integral water basin, according to embodiments of the present invention. A larger view of integral water basin 14 is shown in FIG. 5B.

Figure 6A:
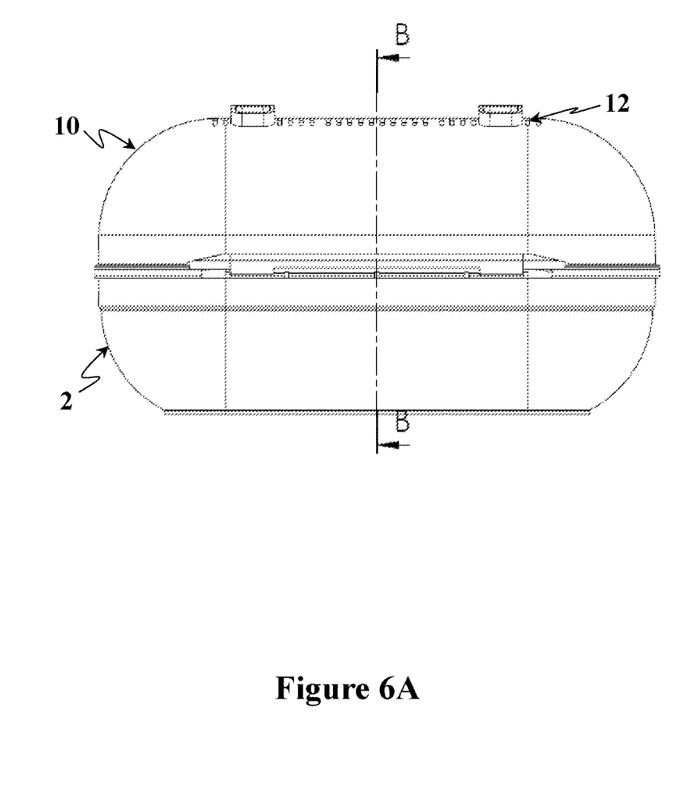
FIG. 6A depicts a side view of the fully-closed fabric sterilization unit of FIG. 1A with section line B-B, according to embodiments of the present invention.
Figure 6B:
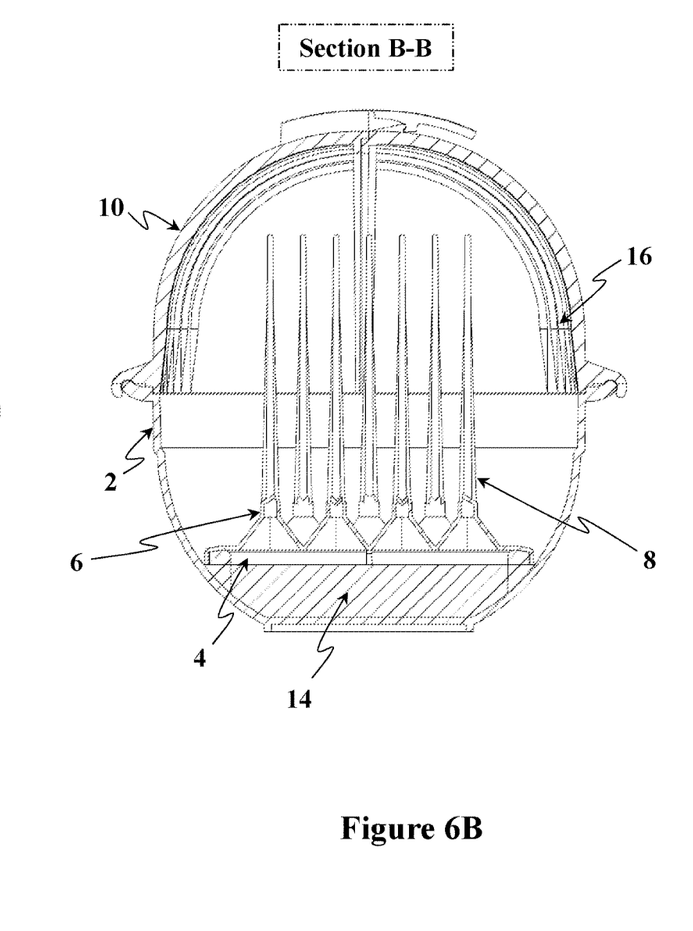
FIG. 6B depicts a section view of the fabric sterilization unit of FIG. 6A along section line B-B, according to embodiments of the present invention.

FIG. 6A depicts a side view of the fully-closed fabric sterilization unit of FIG. 1A with section line B-B, according to embodiments of the present invention. FIG. 6B depicts a section view of the fabric sterilization unit of FIG. 6A along section line B-B, according to embodiments of the present invention. Integral water basin 14 can be seen below nozzle array plate 4. Optional formed drainage ridges 16 can be seen operationally positioned to wick away any liquid water that forms on canopy cover 10 toward the walls of fabric sterilization unit 2 during operation, preventing droplets from dripping onto the fabric material below (not shown).

Figure 7A:
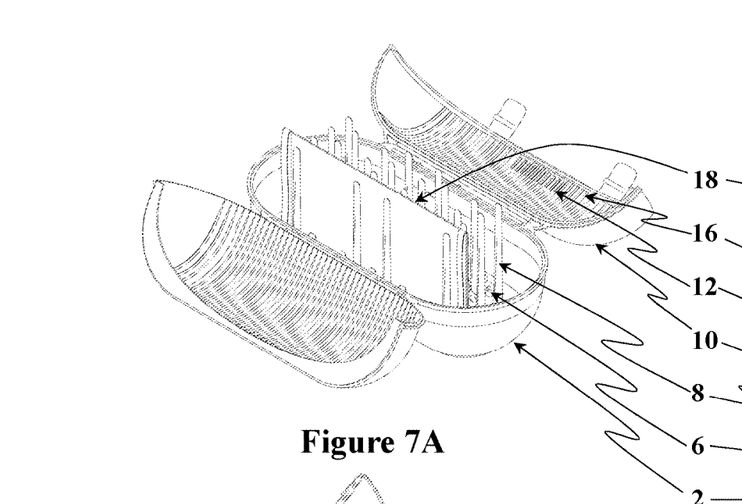
FIG. 7A depicts a perspective view of the fully-open fabric sterilization unit of FIG. 1A with an individually-positioned fabric material shown, according to embodiments of the present invention.
Figure 7B:
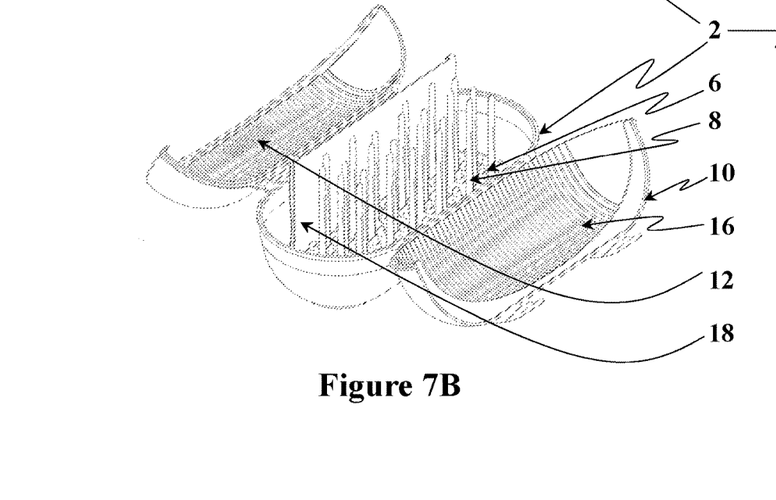
FIG. 7B depicts an alternate perspective view of the fully-open fabric sterilization unit of FIG. 1A with an individually-positioned fabric material shown, according to embodiments of the present invention.
Figure 7C:
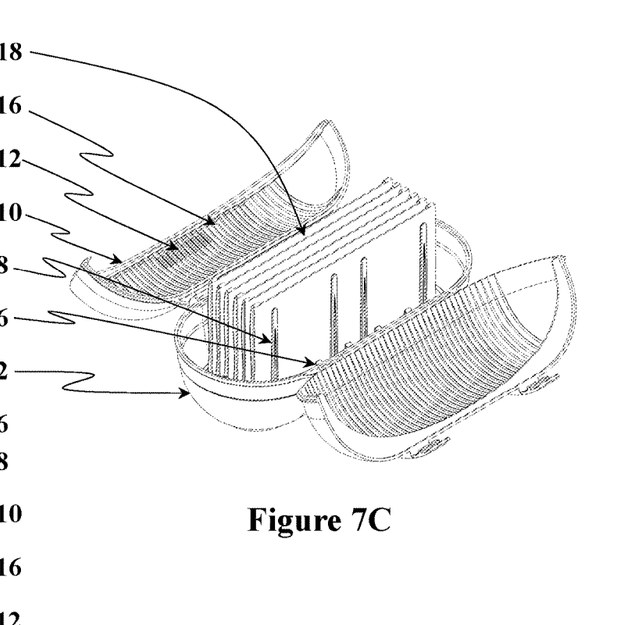
FIG. 7C depicts a perspective view of the fully-open fabric sterilization unit of FIG. 1A with multiple individually-positioned fabric materials shown, according to embodiments of the present invention.

FIG. 7A depicts a perspective view of the fully-open fabric sterilization unit of FIG. 1A with an individually-positioned fabric material shown, according to embodiments of the present invention. FIG. 7B depicts an alternate perspective view of the fully-open fabric sterilization unit of FIG. 1A with an individually-positioned fabric material shown, according to embodiments of the present invention. An individually-positioned fabric material 18 is shown in FIGS. 7A and 7B. FIG. 7C depicts a perspective view of the fully-open fabric sterilization unit of FIG. 1A with multiple individually-positioned fabric materials shown, according to embodiments of the present invention.

Fabric sterilization unit 2 enables the simultaneous sterilization and subsequent reuse of a multiplicity of protective facial masks and medical garments without degrading the integrity of the fabric material.

Figure 8:
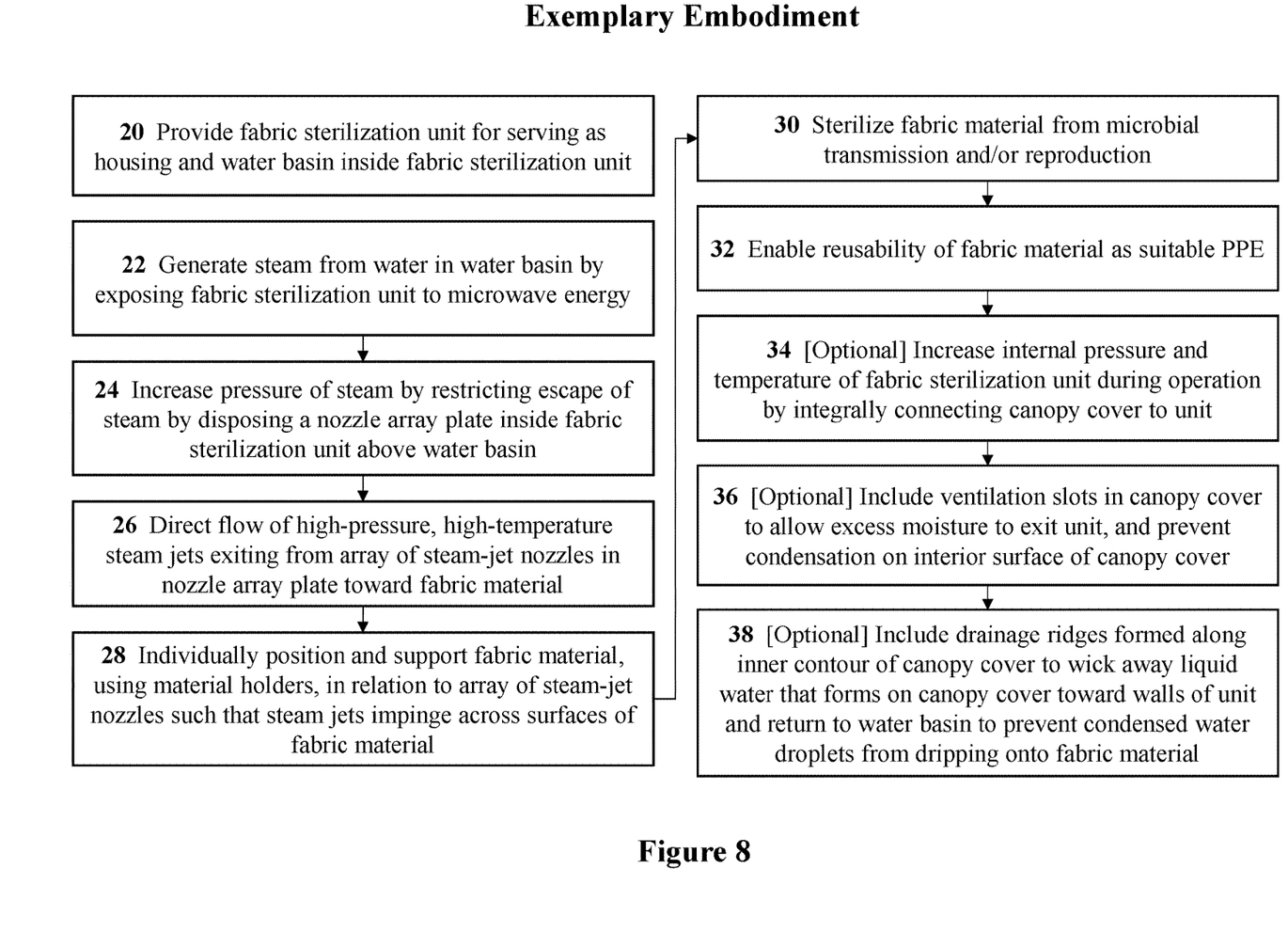
FIG. 8 is a simplified flowchart of the major process steps for sterilizing protective facial masks and medical garments using microwave energy, according to embodiments of the present invention.

FIG. 8 is a simplified flowchart of the major process steps for sterilizing protective facial masks and medical garments using microwave energy, according to embodiments of the present invention. The process starts with providing a fabric sterilization unit for serving as a housing and a water basin inside the fabric sterilization unit (Step 20). The fabric sterilization unit is then used to generate steam from water in the water basin by exposing the fabric sterilization unit to the microwave energy (Step 22). The pressure of the steam is increased by restricting escape of the steam by disposing a nozzle array plate inside the fabric sterilization unit above the water basin (Step 24). A flow of high-pressure, high-temperature steam jets exiting from an array of steam-jet nozzles in the nozzle array plate is then directed toward at least one fabric material (Step 26).

The fabric material is then individually positioned and supported, using material holders, in relation to the array of steam-jet nozzles such that the high-pressure, high-temperature steam jets impinge across the surfaces of at least one fabric material (Step 28). The fabric material is sterilized from microbial transmission and/or reproduction (Step 30), enabling reusability of the fabric material as suitable PPE (Step 32).

Optionally, the internal pressure and internal temperature of the fabric sterilization unit is increased during operation by integrally connecting a canopy cover to the fabric sterilization unit (Step 34). The optional inclusion of ventilation slots in the canopy cover allow excess moisture to exit the fabric sterilization unit during operation, and prevent condensation on the interior surface of the canopy cover (Step 36). The further optional inclusion of drainage ridges formed along the inner contour of the canopy cover wicks away any liquid water that forms on the canopy cover toward the walls of the fabric sterilization unit and returning to the water basin during operation in order to prevent any condensed water droplets from dripping onto the fabric material (Step 38).

While the present invention has been described with respect to a limited number of embodiments, it will be appreciated that many variations, modifications, and other applications of the present invention may be made.

What is claimed is:

1. A device for sterilizing protective facial masks and medical garments using microwave energy, the device comprising:
   (a) a fabric sterilization unit for serving as a housing;
   (b) a water basin disposed inside said fabric sterilization unit, said water basin configured for generating steam from water in said water basin when exposed to the microwave energy;
   (c) a nozzle array plate disposed inside said fabric sterilization unit above said water basin, said nozzle array plate configured for increasing the pressure of said steam by restricting escape of said steam;
   (d) an array of steam-jet nozzles configured for directing a flow of high-pressure, high-temperature steam jets exiting from said steam-jet nozzles toward at least one fabric material, wherein said steam-jet nozzles have angled upper sections to constrict said high-pressure, high-temperature steam jets to be free of any liquid water droplets upon exiting due to the high-pressure differential between said water basin below said nozzle array plate and the interior of said fabric sterilization unit above said nozzle array plate; and
   (e) material holders for individually positioning and supporting said at least one fabric material in relation to said array of steam-jet nozzles adapted such that said high-pressure, high-temperature steam jets impinge across the surfaces of said at least one fabric material for:
      (i) sterilizing said at least one fabric material from microbial transmission and/or reproduction; and
      (ii) enabling reusability of said at least one fabric material as suitable Personal Protective Equipment (PPE).

2. The device of claim 1, wherein said water basin is an integral component of said fabric sterilization unit.

3. The device of claim 1, wherein said fabric sterilization unit and said material holders are adapted for accommodating and supporting said at least one fabric material as a constituent of a surgical mask.

4. The device of claim 1, wherein said angled upper sections of said steam-jet nozzles are further configured to prevent undesirable circulation currents to form in said flow during operation.

5. The device of claim 1, wherein said high-pressure, high-temperature steam jets are adapted to perform said sterilizing without burning, singeing, wetting, or otherwise compromising said at least one fabric material.

6. The device of claim 1, the device further comprising:
   (f) a canopy cover integrally connected to said fabric sterilization unit, said canopy cover configured for increasing the internal pressure and internal temperature of said fabric sterilization unit during operation.

7. The device of claim 6, wherein said canopy cover includes at least one ventilation slot configured for:
   (i) allowing excess moisture to exit said fabric sterilization unit during operation; and
   (ii) preventing condensation on the interior surface of said canopy cover.

8. The device of claim 6, wherein said canopy cover includes at least one drainage ridge formed along the inner contour of said canopy cover, and wherein said at least one drainage ridge configured for wicking away any liquid water that forms on said canopy cover toward the walls of said fabric sterilization unit and returning to said water basin during operation in order to prevent any condensed water droplets from dripping onto said at least one fabric material during operation.

9. The device of claim 6, wherein said canopy cover is adapted to remove excess humidity as gaseous moisture from the interior of said fabric sterilization unit due to the relatively lower temperature of the surfaces of said fabric sterilization unit relative to said internal temperature of said steam generated by said microwave energy.

10. A method for sterilizing protective facial masks and medical garments using microwave energy, the method comprising the steps of:
   (a) providing a fabric sterilization unit for serving as a housing and a water basin inside said fabric sterilization unit;
   (b) generating steam from water in said water basin by exposing said fabric sterilization unit to the microwave energy;
   (c) increasing the pressure of said steam by restricting escape of said steam by disposing a nozzle array plate inside said fabric sterilization unit above said water basin;
   (d) directing a flow of high-pressure, high-temperature steam jets exiting from an array of steam-jet nozzles in said nozzle array plate toward at least one fabric material, wherein said steam-jet nozzles have angled upper sections to constrict said high-pressure, high-temperature steam jets to be free of any liquid water droplets upon exiting due to the high-pressure differential between said water basin below said nozzle array plate and the interior of said fabric sterilization unit above said nozzle array plate; and (e) individually positioning and supporting said at least one fabric material, using material holders, in relation to said array of steam-jet nozzles such that said high-pressure, high-temperature steam jets impinge across the surfaces of said at least one fabric material;

(f) sterilizing said at least one fabric material from microbial transmission and/or reproduction; and (g) enabling reusability of said at least one fabric material as suitable Personal Protective Equipment (PPE).

11. The method of claim 10, wherein said water basin is an integral component of said fabric sterilization unit.

12. The method of claim 10, wherein said fabric sterilization unit and said material holders are adapted to accommodate and support at least one fabric material as a constituent of a surgical mask.

13. The method of claim 10, wherein said angled upper sections of said steam-jet nozzles are further configured to prevent undesirable circulation currents to form in said flow during operation.

14. The method of claim 10, wherein said step of sterilizing said at least one fabric material is performed without burning, singeing, wetting, or otherwise compromising said at least one fabric material.

15. The method of claim 10, the method further comprising the step of:

(h) increasing the internal pressure and internal temperature of said fabric sterilization unit during operation by integrally connecting a canopy cover to said fabric sterilization unit.

16. The method of claim 15, wherein said canopy cover includes at least one ventilation slot configured for:

(A) allowing excess moisture to exit said fabric sterilization unit during operation; and (B) preventing condensation on the interior surface of said canopy cover.

17. The method of claim 15, wherein said canopy cover includes at least one drainage ridge formed along the inner contour of said canopy cover, and wherein said at least one drainage ridge is configured for wicking away any liquid water that forms on said canopy cover toward the walls of said fabric sterilization unit and returning to said water basin during operation in order to prevent any condensed water droplets from dripping onto said at least one fabric material.

18. The method of claim 15, wherein said canopy cover is adapted to remove excess humidity as gaseous moisture from the interior of said fabric sterilization unit due to the relatively lower temperature of the surfaces of said fabric sterilization unit relative to said internal temperature of said steam generated by said microwave energy.

* * * * *